United States Patent [19]

Green

[11] Patent Number: 4,862,901
[45] Date of Patent: Sep. 5, 1989

[54] PROPHYLAXIS

[76] Inventor: Ivan L. Green, 155 W. 68 St., New York, N.Y. 10023

[21] Appl. No.: 171,676
[22] Filed: Mar. 21, 1988
[51] Int. Cl.$^4$ .............................................. A61F 5/42
[52] U.S. Cl. .................................. 128/830; 128/844; 604/347
[58] Field of Search ................ 128/132 R, 830, 844; 604/347, 353, 349

[56] References Cited

U.S. PATENT DOCUMENTS

| D. 288,485 | 2/1987 | Denno | D24/51 |
|---|---|---|---|
| 2,591,783 | 7/1952 | Craddock | 604/353 |
| 3,536,066 | 10/1970 | Ludwig | 128/132 R |
| 3,996,930 | 12/1976 | Sekulich | 128/79 |
| 4,488,541 | 12/1984 | Garcia | 128/79 |
| 4,553,968 | 11/1985 | Komis | 604/349 |
| 4,664,104 | 5/1987 | Jaicks | 604/353 X |
| 4,807,611 | 2/1989 | Johnson | 128/844 |

Primary Examiner—Dalton L. Truluck
Attorney, Agent, or Firm—Natter & Natter

[57] ABSTRACT

A prophylaxis suitable for women is configured as wearing apparel. The apparel comprises a panty having an upper fabric portion and a lower portion. The lower portion includes a thin flexible liquid impervious membrane which registers with and covers the front and rear crotch area of the wearer. A closed ended tubular extension is formed of one piece with the membrane and is adapted to be inserted into the wearer's vaginal cavity.

20 Claims, 3 Drawing Sheets

PROPHYLAXIS

BACKGROUND OF THE INVENTION

1. Field of the Invention

The invention relates generally to contraceptives and/or prophylactic devices and more particularly to those which provide barriers against bodily fluid transmission.

2. Related Art

There has been a recent resurgence in the use of condoms caused by the spread of a relatively new a virulent venereal disease, i.e. AIDS, which has reached epidemic levels. Health authorities have advocated the utilization of condoms to prevent the sexual transmission of the virus during intercourse. Despite warnings and public announcements many people with active sex lives have shunned the use of condoms.

There have been many reasons for the negative attitudes towards condom usage. One reason may have been the inconvenience of having to interrupt the natural sequence of sexual foreplay to apply the condom and the inconvenience of the removal requirements. Another factor was the conflicting opinions of medical experts as to their efficacy in preventing the transmission of viral diseases including herpes and AIDS. Further, some health experts have stated that the average male does not properly apply or use condoms. Others believed that certain condoms such as those with natural membranes were permeable to the AIDS virus and could not be relied upon as an effective preventative.

Studies have apparently indicated that even with proper condom usage, seminal fluid could still manage to come in contact with vaginal and other body parts. U.S. Pat. No. 2,591,783 issued Apr. 8, 1952 to D. L. Craddock acknowledged this phenomenon and suggested an apron shield for use with a condom. An aperture having an annular flange was provided through the shield. A condom distended through the aperture with the upper condom portion rolled beneath the flange. Such structure was awkward and was apparently never commercialized. Like conventional condoms, it could only be applied after the male organ was erect. In addition, however, the device required several awkward extra physical steps which detracted from not only the natural sequence of events but with the conventional condom application procedures.

In addition to the confusing medical advice was the admonishment of various religious authorities with respect to the usage of male sexual barriers. Another drawback against acceptance of condom usage was that despite liberal sexual attitudes and the declared equality among sexes, the mechanical aspects of usage, hence the ultimate election to use, was solely in the control of only one, i.e. the male, partner.

In view of all of these disadvantages, the present invention seeks to provide a new concept in prophylactic devices for both conception and disease control.

SUMMARY OF THE INVENTION

In compendium, the invention comprises a prophylactic configured as an undergarment, e.g., a panty. The panty includes a fluid impermeable membrane which is shaped to be registered with the front and rear crotch areas of the wearer. In addition, an elasticized top band is provided and a fabric portion may extend between the membrane and the top band.

The fluid impermeable membrane may be comprised of a thin flexible film of latex or other material. Registered with the wearer's vaginal opening is a tubular condom like extension formed in one piece with the membrane. The extension is inserted into the vaginal cavity and may include annular folds to facilitate distension into the cavity. It is preferably lubricated and of sufficient strength to withstand the rigors of intended application.

From the foregoing summary, it will be appreciated that it is an aspect of the present invention to provide a prophylaxis which is not subject to the disadvantages of the related art aforementioned.

Another aspect of the present invention is to provide a prophylaxis of the general character described which furnishes a more complete barrier to the transmission of bodily fluids then heretofore available.

A feature of the present invention is to provide a prophylaxis of the general character described which is employable without interruption of sexual activities such as foreplay.

A consideration of the present invention is to provide a prophylaxis of the general character described the usage of which is within the control of the female rather than the male partner.

A further consideration of the present invention is to provide a prophylaxis of the general character described which provides a more efficacious barrier against socially transmitted diseases.

Yet another feature of the present invention is to provide a prophylaxis of the general character described which forms part of and may be worn as an undergarment and is thus not subject to the possibility of being lost or forgotten.

Another feature of the present invention is to provide a prophylaxis of the general character described which forms part of an undergarment and is thus unobtrusive, attractive in appearance and minimizes embarrassment.

Other aspects, features and considerations of the invention in part will be obvious and in part will be pointed out hereinafter.

With these ends in view, the invention finds embodiment in certain combinations of elements, arrangements parts and series of steps which will be exemplified in the prophylaxis hereinafter described with reference to the accompanying drawings and the scope of which is more particularly pointed out and indicated in the appended claims.

BRIEF DESCRIPTION OF THE DRAWINGS

In the accompanying drawings in which is shown some of the various possible exemplary embodiments of the invention.

DESCRIPTION OF THE PREFERRED EMBODIMENTS

Figure 1:
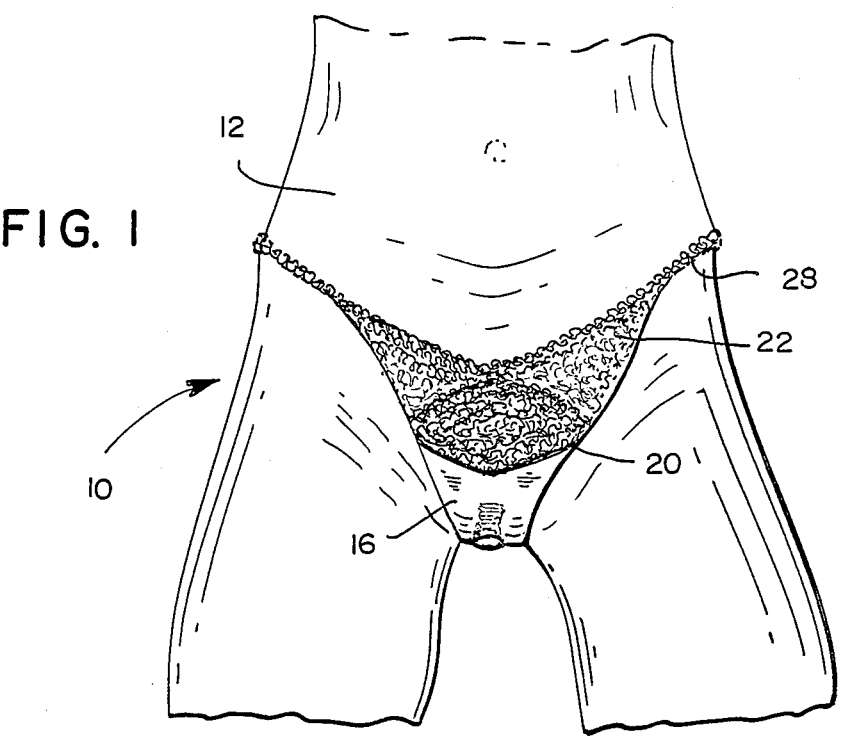
FIG. 1 is a fragmentary plan or elevational view of a female wearing a prophylaxis constructed in accordance with an embodying the invention and showing a front view of a panty including a fluid impermeable membrane disposed over the wearer's front crotch area.

Referring now in detail to the drawings, the reference numeral 10 denotes generally a prophylaxis constructed in accordance with an embodying the invention. The prophylaxis 10 is configured in the overall shape of a panty and is shown in the illustration of FIG. 1 being worn as an undergarment by a female person 12.

Figure 5:
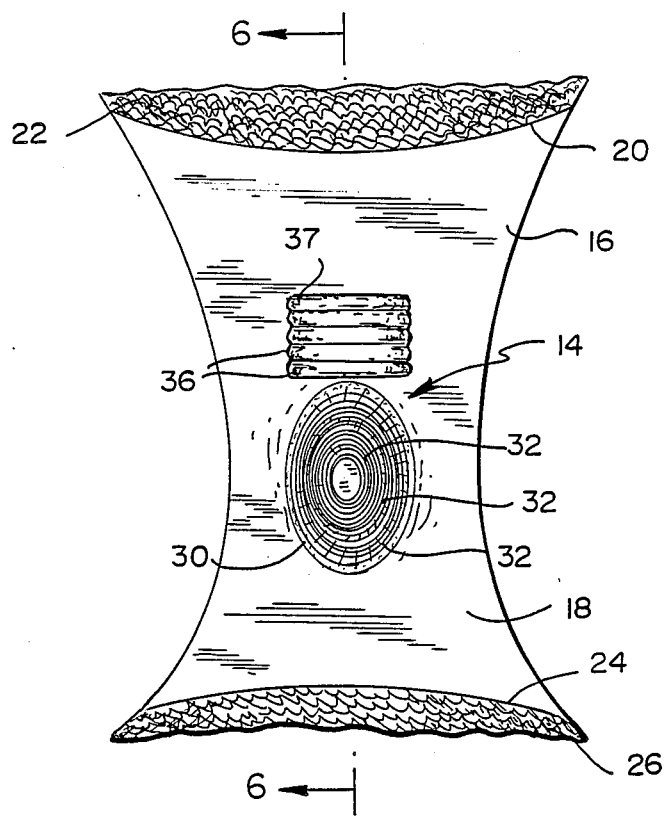
FIG. 5 is a fragmentary plan view of the membrane and showing an array of ribs provided on the membrane adjacent the tubular extension.

Pursuant to the present invention, the prophylaxis 10 includes a thin flexible fluid impermeable membrane 14 having a substantially hourglass plan configuration as illustrated in FIG. 5. The membrane 14 includes a substantially triangular front portion 16 and a rear portion 18. The membrane 14 is preferably formed of a flexible fluid impervious material such as latex of a thickness substantially that of a conventional condom. Secured to an upper edge 20 of the front portion 16 is a fabric panel 22 which may be formed of lace type fabric or any other conventional fabric either of synthetic or natural fiber. Similarly secured to an upper edge 24 of the rear portion 18 is a rear fabric panel 26. The fabric panels 22, 26 may be joined to the membrane 14 by adhesives, bonding, heat sealing, stitching, or by being molded into the membrane.

In order to maintain the prophylaxis 10 in wearing position about the wearer, an elastic top band 28 is joined to the upper edges of both the front and rear fabric panels. The band 28 is adapted to encircle the wearer's lower torso as illustrated in FIG. 1. To don the prophylaxis, one leg of the wearer is inserted in each of the spaces between the band and the membrane with the front portion 16 facing forward. The panty is then pulled up so that the portions 16, 18 are registered with and are juxtaposed against their associated body parts.

Figure 6:
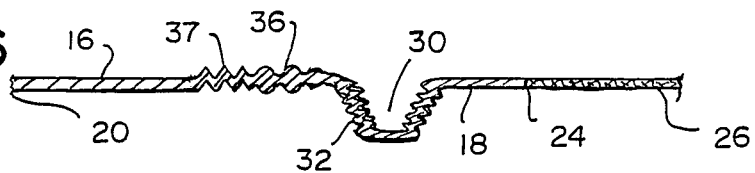
FIG. 6 is an enlarged scale sectioned view through the membrane, the same being taken substantially along the line 6—6 of FIG. 5 to more clearly illustrate the ribs.

In accordance with the invention, the membrane 14 includes, in the area registered with the vaginal cavity 34 of the wearer, an integral one piece unitarily formed tubular condom like extension 30 having a closed distal end. The extension is adapted to be inserted into the vaginal cavity 34 and may include a plurality of annular pleats or folds 32 which may be of equal or of successively decreasing diameter as shown in FIGS. 5 and 6.

Figure 3:
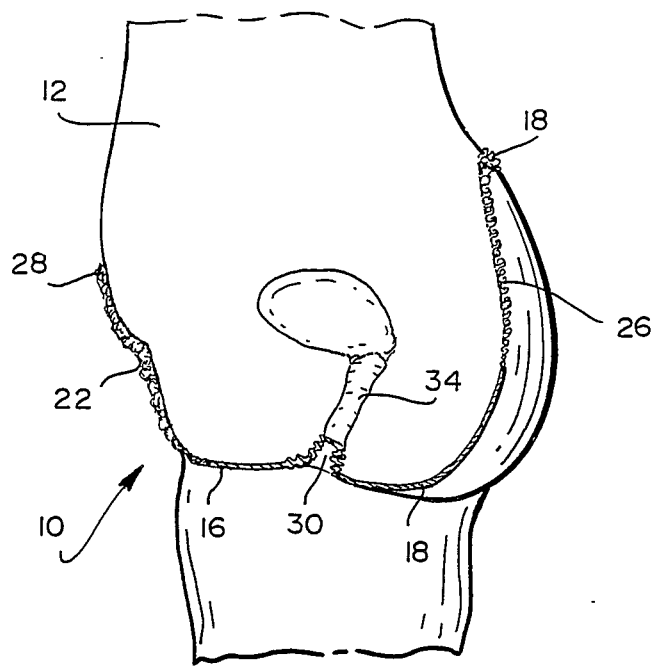
FIG. 3 is an longitudinal cross-sectional view through the wearer's lower torso, with unrelated anatomical elements deleted for clarity, and showing the tubular extension in an unextended, folded position, lying within the mouth of the vaginal cavity.
Figure 4:
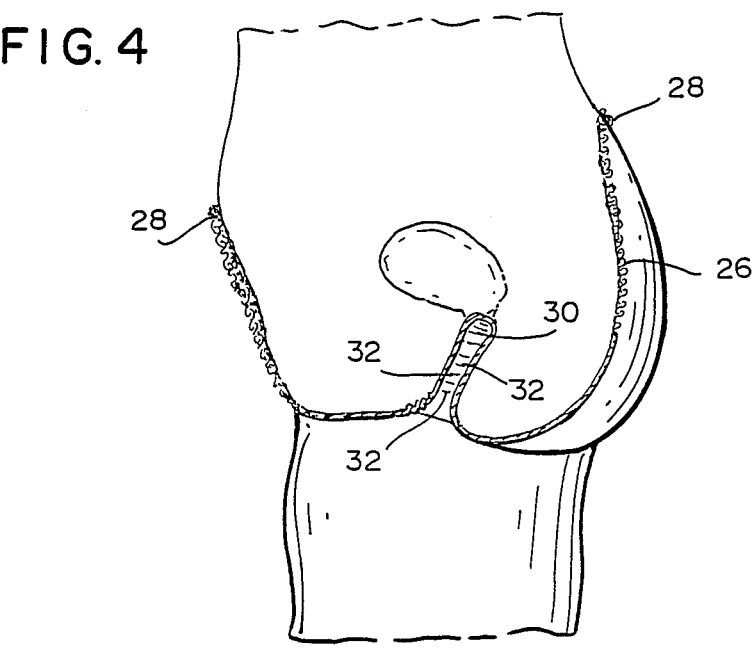
FIG. 4 is a sectional view similar to that of FIG. 3 yet showing the tubular extension within the vaginal cavity.

Referring now to FIG. 3, the prophylaxis 10 is shown worn by the female person 12 with the extension 30 positioned in registry with and slightly entering the vaginal cavity 34. The width and depth of the extension 30 is sufficient to accommodate insertion of the extension 30 into the cavity 34 to a position shown generally in FIG. 4 ready to receive a male organ during intercourse.

Distension of the extension 30 into the cavity 34 may be accomplished either when the prophylaxis 10 is donned, or prior to intercourse using fingers, an insertion tool or it may be inserted by the male organ during commencement of intercourse.

The extension 30 is lubricated on its interior surface adapted to receive the male organ since it preferably remains in the vaginal cavity during intercourse. For such reason, the extension 30 may be of a thickness and strength greater than that of a conventional condom without loss of male sensitivity. The extension 30 may additionally include a lubricant on its exterior surface which is adapted to abut the walls of the vaginal cavity for facilitating insertion.

As previously mentioned, the extension and membrane 14 are preferably formed of unitary one piece construction of latex or other material which is conventionally used in condom fabrication. The front and rear portions 16, 18 of the membrane 14 not only serve to maintain the extension 30 in position prior to intercourse but, in addition, provide an added barrier against the transmission of fluids which may escape from the extension.

Figure 2:
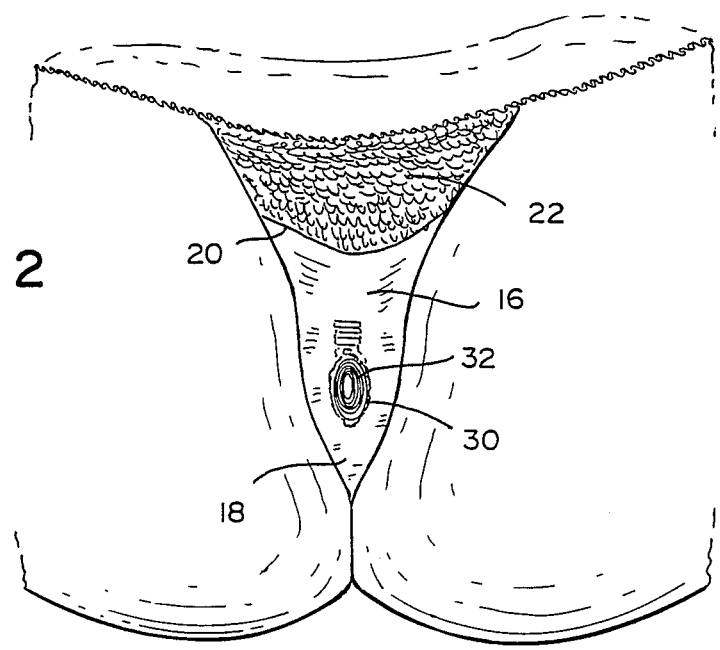
FIG. 2 is a fragmentary bottom plan view of the wearer's crotch area, in enlarged scale and more clearly illustrating the membrane and a unitary tubular extension adapted to be inserted into the vaginal cavity.
Figure 7:
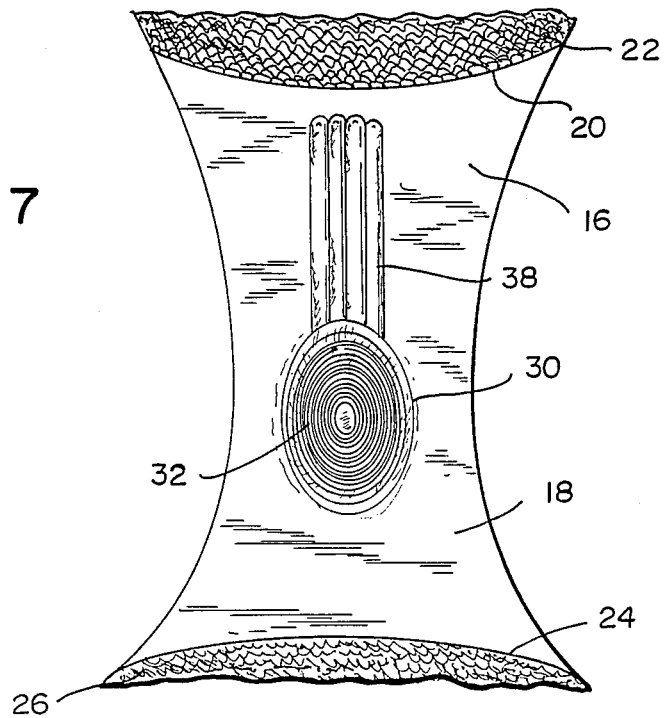
FIG. 7 is a plan view of a membrane similar to that of FIG. 5 but of and alternate embodiment wherein a different array of ribs has been provided.

It should be noted from an examination of FIGS. 1, 2 and 5 that a plurality of transverse thickened ribs 36 and/or folds 37 may be provided along the longitudinal axis of the front portion 16. As illustrated in an alternate embodiment shown in FIG 7, a plurality of thickened vertical ribs 38 may be provided. The ribs 36, 38 or folds 37 serve to provide added stimulation for the female wearer 12.

It should also be appreciated that the prophylaxis need not be limited in usage to a female partner but may be worn by a male partner as a condom with the membrane providing an added barrier against fluid transmission.

Thus it will be seen that there is provided a prophylaxis which achieves the various considerations, aspects and features of the present invention and which is well suited to meet the conditions of practical usage.

Having thus described the invention, there is claimed as new and desired to be secured by Letter Patent:

1. A prophylaxis for the prevention of bodily fluid transmission between sexual partners, the prophylaxis comprising a thin flexible fluid impermeable membrane configured to overlie portions of the front and rear crotch area of a female wearer, without extending beyond such crotch area, the membrane including a thin flexible fluid impermeable hollow tubular closed ended extension adapted to receive a male organ and adapted to be inserted into a body cavity, the membrane and the tubular extension being formed of one piece unitary construction and providing a barrier against fluid transmission and means for mounting the membrane to the body of the wearer the means for mounting the membrane to the body of the wearer comprising an elastic top band, a breathable fluid permeable fabric panel extending substantially along a top edge of the membrane and between a front portion of the membrane and the top band and means extending between the top band and the rear portion of the membrane whereby an efficacious barrier against fluid transmission is provided and the prophylaxis may be confortably worn for extended periods prior to engagement in sexual relations.

2. A prophylaxis constructed in accordance with claim 1 wherein the membrane is of hourglass configuration.

3. A prophylaxis constructed in accordance with claim 1 wherein the fabric comprises lace.

4. A prophylaxis constructed in accordance with claim 1 wherein the tubular extension includes annular folds whereby when the prophylaxis is worn by a female person and with the extension in registry with a vaginal cavity, the extension will be retained against the cavity.

5. A prophylaxis constructed in accordance with claim 1 wherein the membrane includes transverse ribs in the portion configured to overlie the front crotch area.

6. A prophylaxis constructed in accordance with claim 1 wherein the membrane includes longitudinal ribs in the portion configured to overlie the front crotch area.

7. A method of safe sexual relations with utilizing a prophylaxis constructed in accordance with claim 1, the method comprising the steps of:
   (a) donning the prophylaxis of claim 1, the donning step including,
      (i) inserting each of the wearer's legs between the top band and one side of the membrane, and,
      (ii) pulling the membrane against the crotch area of the wearer, the method of further including the step of:
   (b) inserting a male organ into the tubular extension and,
   (c) inserting the tubular extension into the body cavity.

8. A method in accordance with claim 7 wherein the tubular extension is inserted into the body cavity prior to insertion of the male organ into the extension.

9. A method in accordance with claim 7 wherein the male organ is inserted into the tubular extension prior to inserting the extension into the cavity.

10. A method in accordance with claim 7 wherein the male organ is inserted into the extension and the extension is inserted into the cavity simultaneously.

11. A method in accordance with claim 7 wherein the step of inserting the tubular extension into the body cavity comprises inserting the extension into a vaginal cavity.

12. A prophylaxis constructed in accordance with claim 1 further including an additional breathable fluid permeable fabric panel, the additional panel extending between a rear portion of the membrane and the top band.

13. A prophylaxis constructed in accordance with claim 12 wherein the fabric panels are joined to the membrane by an adhesive.

14. A prophylaxis constructed in accordance with claim 12 wherein the fabric panels are joined to the membrane by bonding.

15. A prophylaxis constructed in accordance with claim 13 wherein the fabric panels are joined to the prophylaxis by being heat sealed.

16. A prophylaxis constructed in accordance with claim 13 wherein the fabric panels are joined to the membrane by stitches.

17. A prophylaxis constructed in accordance with claim 13 wherein the membrane is formed by molding, the fabric panels being joined to the membrane during molding.

18. A prophylaxis for a female which can be worn as a garment, the prophylaxis comprising a thin, flexible fluid impervious membrane adapted to be disposed about and overlie only the crotch area of a female wearer, a tubular extension having a closed distal end, the extension being positioned in a mid portion of the membrane and being adapted to be disposed in registry with the wearer's vaginal cavity, the extension being formed of one piece construction with the membrane, the extension being dimensioned for insertion into the vaginal cavity and to accommodate a male organ, the prophylaxis further including a top band adapted to maintain the membrane in position both as an undergarment and during sexual intercourse and a breathable fluid permeable fabric panel, the panel extending substantially across a top edge of the membrane, the panel interconnecting the top band and a front portion of the membrane and means interconnecting a rear portion of the membrane with the top band.

19. A prophylaxis constructed in accordance with claim 18 wherein the extension includes expandable pleats to facilitate distention within the vaginal cavity.

20. A prophylaxis constructed in accordance with claim 18 further including an additional fluid permeable fabric panel interconnecting the top band and the membrane, one fabric panel extending across the front of the wearer and the other extending across the rear of the wearer.

* * * * *